US006919198B1

(12) United States Patent
Korpela et al.

(10) Patent No.: US 6,919,198 B1
(45) Date of Patent: Jul. 19, 2005

(54) MICROBIAL PROTEIN EXPRESSION SYSTEM

(75) Inventors: Timo Korpela, Turku (FI); Sheila Macintyre-Ayane, Reading (GB); Anton Zavialov, Moscow (RU); Natalia Battchikova, Turku (FI); Lada Petrovskaya, Moscow (RU); Vladimir Zav'yalov, Moscow (RU); Vyacheslav Korobko, deceased, late of Moscow (RU); Galina Petrovna Korobko, legal representative, Moscow (RU)

(73) Assignee: Biotecnol S.A., Oeiras (PT)

( * ) Notice: Subject to any disclaimer, the term of this patent is extended or adjusted under 35 U.S.C. 154(b) by 0 days.

(21) Appl. No.: 09/959,650

(22) PCT Filed: May 3, 2000

(86) PCT No.: PCT/FI00/00387

§ 371 (c)(1), (2), (4) Date: Feb. 26, 2002

(87) PCT Pub. No.: WO00/66756

PCT Pub. Date: Nov. 9, 2000

(30) Foreign Application Priority Data

May 4, 1999 (FI) ................................................ 991014

(51) Int. Cl.[7] .......................... C12N 1/21; C12N 15/00; C07H 21/04

(52) U.S. Cl. ............................. 435/252.33; 435/252.3; 435/69.1; 536/23.4; 536/23.5

(58) Field of Search ......................... 435/252.3, 252.33; 536/23.4, 23.5

(56) References Cited

FOREIGN PATENT DOCUMENTS

| | | |
|---|---|---|
| EP | 0 774 512 A2 | 5/1997 |
| EP | 0 885 967 A2 | 12/1998 |
| WO | WO 94/08012 | 4/1994 |
| WO | WO 96/14422 | 5/1996 |

OTHER PUBLICATIONS

Stentebjerg–Olesen et al., Microbiology 143, pp. 2027–2038 (1997).*
Pallesen et al., Microbiology 141, pp. 283902848 (1995).*
Xu et al., Molecular Microbiology 16(5), pp. 1011–1020 (1995).*
D. A. G. Chapman et al., Journal of Bacteriology, vol. 181, No. 8, Apr. 1999, pp. 2422–2429.
V. P. Zav'yalov et al., Biochem. J. (1997) 324, 571–578.
T. A. Rapoport et al., Annu. Rev. Biochem. 1996, 65:271–303.
G. Schatz et al., Science, vol. 271, pp. 1519–1526, Mar. 15, 1996.
C. Santini et al., The EMBO Journal, vol. 17, No. 1, pp. 101–112, 1998.
J. H. Weiner et al., Cell, vol. 93, 93–101, Apr. 3, 1998.
C. A. Lunn et al., The Journal of Biological Chemistry, vol. 257, No. 19, pp. 11424–11430, Oct. 10, 1982.
A. El Yaagoubi et al., Journal of Bacteriology, vol. 176, No. 22, Nov. 1994, p. 7074–7078.
G. R. Jacobson et al., Biochemistry, vol. 15, No. 11, pp. 2297–2303, Nov. 11, 1976.
F. M. Hantash et al., Microbiology (1997) 143, 147–156.
G. P. Rigg et al., Microbiology (1998) 144, 2905–2914.
E. Joseph–Liauzun et al., Gene, 86 (1990) 291–295.
D. Missiakas et al., Journal of Bacteriology, vol. 179, No. 8, Apr. 1977, 2465–2471.
G. Georgiou et al., Trends in Biology (1993) 11:6–10.
T. Klauser et al., The EMBO Journal, vol. 9, No. 6, pp. 1991–1999, 1990.
C. Stathopoulos et al., Appl. Microbiol. Biotechnol. (1996) 45:112–119.
STIN International, File MEDLINE, MEDLINEaccession No. 96170663, vol. 21, No. 12, pp. 912–919 (1995).
Perez et al., Biochemical and Biophysical Research Communications, vol. 210, No. 2, pp. 524–529 (1995).

* cited by examiner

*Primary Examiner*—Terry McKelvey
*Assistant Examiner*—Nancy T. Vogel
(74) *Attorney, Agent, or Firm*—Birch, Stewart, Kolasch & Birch, LLP

(57) ABSTRACT

The present invention provides bacterial strains for secretion of soluble biologically active recombinant heterologous proteins into periplasm or on a surface/into a cultivation medium of bacteria. The invention exploits the secretion system of Gram-negative bacteria including periplasmic chaperones and usher/secretin proteins. For accomplishing the aim, the bacterial strains simultaneously express the fusion protein (signal peptide)-(mature hecterologous protein)-(subunit of a bacterial surface structure, Caf1), periplasmic chaperone specific for the subunit, and outer membrane usher/secretin protein specific for the subunit. Secretion of fusion proteins: (signal peptide of Caf1)-(mature human IL-1β)-(mature Caf1), (signal peptide of Caf1)-(mature human GM-CSF)-(mature Caf1), and (signal peptide of Caf1)-(mature human IL-1ra)-(mature Caf1) that were expressed in *Escherichia coli* simultaneously with the periplasmic chaperone Caf1M and the usher/secretin protein Caf1A are examples of the use of the invention.

6 Claims, 14 Drawing Sheets

1 2 3 4 5 6 7 8 9 10

1 2 3 4 5 6 7 8 9 10

| Number | Amino acid |
|---|---|
| 1 | Ala |
| 2 | Pro |
| 3 | Val |
| 4 | Arg |
| 5 | Ser |

MICROBIAL PROTEIN EXPRESSION SYSTEM

This application is the national phase under 35 U.S.C. § 371 of PCT International Application No. PCT/FI00/00387 which has an International filing date of May 3, 2000, which designated the United States of America and was published in English.

FIELD OF INVENTION

This invention is related to biotechnology and more specifically to production of recombinant heterologous proteins by microbes. In particular, this invention concerns secretion of soluble biologically active heterologous proteins into periplasm and/or on a surface/into a cultivation medium of Gram-negative bacteria. The invention exploits the secretion system of Gram-negative bacteria including periplasmic chaperones and usher/secretin proteins of the system.

BACKGROUND OF INVENTION

Commercial production of various medically and industrially valuable recombinant proteins by microbes is one the key challenges of modem biotechnology. Even though such systems are known, there are severe technical problems which are encountered within large-scale exploitation of microbial cell machinery. There are several secretion systems in Gram-negative bacteria which can be potentially exploited for secretion of recombinant heterologous proteins. The systems are briefly reviewed below.

1. Secretion Across the Inner Membrane

The majority of secreted proteins in *Escherichia coli* are synthesized as precursors with a classic N-terminal signal peptide (SP) which is essential for efficient export and which is cleaved during or following translocation across the inner membrane. Translocation is mediated by the Sec translocase (SecA/Y/G/E). SecA is a peripherally associated ATPase, which interacts with the signal sequence and mature part of the precursor, guides the polypeptide into the translocator and provides energy for the process. Sec Y, E and G are integral membrane proteins that form the translocator itself and a central aqueous channel through which the polypeptide is translocated. SecD and F have large periplasmic domains. Proposed functions of these two proteins are related to later steps in the process and have included release from the membrane and mediation of transfer of energy from the proton motive force. Polypeptides are translocated in an 'unfolded' state. Hence SecB is a cytosolic chaperone apparently dedicated to the secretion pathway which is required for export of a subset of secreted proteins. SecB both inhibits premature folding and targets the precursor to the membrane translocase complex. It now appears that basic principles of the export system are universal. Although translocation is primarily co-translational in eukaryotic systems and targeting to the secretion apparatus is primarily via SRP (signal recognition particle), the core translocator is homologous in both systems (yeast Sec 61 $\alpha$ and $\gamma$ are homologous of *E. coli* SecY/E). Also, *E. coli* ffh and 4.5S RNA are homologous of eukaryotic 54 KD subunit and 7S RNA of SRP, respectively. Comparison of the eukaryotic and prokaryotic systems has been extensively reviewed recently (Rapoport, T., et al. (1996)Annual Review of Biochemistry. 65:271–303; Schatz, G., and B. Dobberstein (1996)Science. 271:1519–1526).

Similarities in the basic function of eukaryotic and bacterial export systems have meant that some mammalian proteins can be successfully secreted to the periplasm of *E. coli*. Examples include human insulin. Often, however, fine tuning is required such as optimising the N-terminus of the mature protein, removal of positively charged residues at the end of the SP or beginning of the mature protein, ensuring presence of a good cleavage site. Frequently, a bacterial signal peptide such as the OmpA SP has been used. The Caf1 signal sequence has also been successfully used to export mammalian cytokines (see below). A major problem on recombinant expression in *E. coli* is incorrect folding with accompanying protein degradation or accumulation in an insoluble and inactive form as inclusion bodies.

In addition to the sec dependent secretion system there are at least two other systems of protein translocation across the bacterial inner membrane. The M13 phage coat protein is also synthesised with an additional SP, but assembly of this protein across the membrane is independent of the sec machinery. Recently, a novel pathway involved in secretion of cofactor-containing proteins has been elucidated (Santini, G., et al. (1998) EMBO Journal, 17:101–112; Weiner, J., et al. (1998) Cell. 93:93–101). Proteins following this pathway have a long leader containing a characteristic 'twin arginine' motif. It is proposed that cofactor attachment occurs in the cytosol and that the fully folded protein is translocated across the inner membrane via products of the mttABC operon. In addition, there are cytosolic proteins of *E. coli* which appear to be localised in a priviledged site which is sensitive to osmotic shock. Therefore may have some transient access to the periplasm. Such proteins include thioredoxin (Lunn, C. A., and V. P. Pigiet. (1982) J.Biol.Chem. 257:11424–11430) involved in disulphide reduction of cellular components, the cytosolic chaperone DnaK (Yaagoubi, A.,et al. (1994) Journal of Bacteriology. 176:7074–7078), elongation factor Tu (Jacobson, G., et al. (1976) Biochemistry. 15:2297–2303) and inner membrane bound components of enterobactin synthase complex (Hantash, F., et al. (1997) Microbiology. 143:147–156), and capsule assembly (Rigg, G., et al. (1998) Microbiology. 144:2905–2914).

It has been suggested that this 'compartment' may be related to transient formation of adhesion zones between the bacterial inner and outer membranes, but nothing is known regarding properties of the protein which targets them to this location nor about the physical nature of this 'compartment'. A number of cytosolic recombinant proteins (i.e. without SP) also behave in a similar manner and are thus presumably targeted to the same cellular location. These include GST fusion proteins, interleukin 1$\beta$ (Joseph-Liauzun, E., et al. (1990) Gene. 86:291–295).

2. Extracellular Secretion Systems

Six different pathways for export of extracellular proteins have been identified in Gram negative bacteria. Each pathway has been identified in a diverse range of bacteria. The basic properties of these systems are summarised in FIG. 1 (recently reviewed by Lory (Lory, S. (1998) Current Opinion in Microbiology. 1:27–35).

The Type II pathway, which is considered to be the main terminal branch of the sec- dependent pathway, is used for export of many different unrelated soluble proteins. It involves a folded periplasmic intermediate and requires approximately 12 dedicated genes for export across the OM. Alternative terminal branches to the sec pathway include specific chaperone-dependent fimbriae assembly and the OM helper pathway. The former pathway also involves a periplasmic intermediate (at least partially folded) but in this case the secreted polypeptide is specifically transported in association with its own chaperone/outer membrane usher protein system. Outer membrane helpers fold into the outer membrane with concomitant exposure of the effector domain at the cell surface and, in the case of IgA protease, release via self-hydrolysis. Interaction with general periplasmic chaperones e.g. DsbA has been demonstrated as a critical step in secretion pathway for a number of sec dependent proteins.

Type I, Type III, and most members of Type IV pathways are sec independent and mediate secretion of a specific protein (subset of proteins or DNA (Type IV) directly from the cytosol. Type I results in secretion into the external media, whereas Type III targets the secreted protein directly into the eukaryotic cell following contact-stimulated activation of the secretion system. The Type III pathway also shares many features with flagellar assembly systems.

3. Secretion of Recombinant Heterologous Proteins in Gram-negative Bacteria

Incorrect folding of proteins in the cytosol may lead to degradation or formation of misfolded protein as inclusion bodies. In many instances, therefore, it is desirable to have heterologous expression of recombinant proteins in the bacterial periplasm, at the cell surface, or in the extracellular media, permitting correct folding and formation of a functional product. Proteins secreted to the periplasm of *E. coli* are in an oxidising environment, compared to the reducing environment of the cytosol. The periplasm contains oxidoreductases and chaperones (disulphide bond isomerase, DsbA and C, peptidyl prolyl cis-transisomerase, RotA. SurA, and FkpA) which are essential for the correct folding of proteins (Missiakas. D., and S.Raina. (1997) Journal of Bacteriology 179:2465–2471). In addition, recombinant proteins expressed in the periplasm or secreted to the extracellular medium would represent a high percentage of the final protein content of these respective compartments. Thus, when the final goal is to obtain a purified recombinant product, secretion of the product to the periplasm or externally should greatly facilitate purification protocols. Although there are quite a few systems available for periplasmic localisation of proteins, there is no major system for secretion of extracellular products from *E. coli*. Over the past decade there has also been a great deal of interest in expressing proteins and peptides on the surface of microorganisms. Phage display technology (Winter, G., et al. (1994) Annual Review of Immunology 12:433–455) utilises the coat protein of filamentous bacteriophage for surface display of proteins or peptides. Such technology has been applied to the isolation of specific antibody fragments and for the rapid identification of peptide ligands. Interest in surface display in *E. coli* (Georgiou, G., et al. (1993) Trends in Biotechnology. 11:6–10) and other Gram negative bacteria has centered around identification of protective epitopes and their applications as live vaccines, production of bacterial adsorbents and whole-cell biocatalysts.

Although there has been some success in expressing of proteins, there are a number of limitations within the existing systems as outlined below.

Most secretory/assembly pathways of *E. coli* have been investigated for their potential exploitation as secretion vehicles for heterologous proteins. These include systems that direct the protein to the periplasm, cell surface or extracellular medium.

3.1 SP Alone

A number of expression vectors use a bacterial SP (often that of the OM protein OmpA) to mediate export across the inner membrane. Destination of the protein depends on the nature of the protein itself. It is not uncommon for proteins exported in this way in high levels to form insoluble complexes, inclusion bodies, in the periplasm as a result of incomplete folding.

3.2. Affinity Purification Systems

Fusion expression systems have been developed to facilitate downstream purification of recombinant products. Examples include insertion of a His tag for purification on a Nickel column (Clontech, Qiagen, In vitrogen); fusion to MalE (New England Biolabs), maltose binding protein, with subsequent purification on an amylose column; thioredoxin fusions with PAO (phenyl arsine oxide) resin and chitin binding domain fusions with chitin columns (New England Biolabs). By inclusion or omission of SP in the vector, some of these systems (e.g. MalE, His Tag) can be adapted for periplasmic or cytosolic expression, respectively. In general, such vectors contain a highly specific protease cleavage site for downstream purification of the product. Fusions functional in both domains, e.g. MalE and secreted domain, can be obtained. This, however, is dependent on the nature of the protein. The carrier domain may interfere with folding of the recombinant protein resulting in protein degradation, insolubility of the protein due to membrane association or formation of insoluble inclusion bodies at higher concentrations.

3.3. Surface Display in *E. coli*

Insertion of epitopes into major OM proteins (OmpA, LamB, PhoE), flagella, fimbriae. These systems involve insertion of epitopes into a permissive site, i.e. surface loop within OM proteins or flagellar, fimbriae subunits, without affecting assembly of the membrane protein or surface appendage. In general, there are severe size restrictions of the insert (10–60 amino acids) to avoid effects on folding and assembly of the protein. There are reports of surface display of whole proteins by preparing terminal fusions to part of the outer membrane protein. OmpA or of IgA protease. Using a Lpp- OmpA vector, complete enzymes have been localised to the surface of *E. coli* offering the potential of surface display, but these constructs lead to disruption of the outer membrane with concomitant toxicity to the cell and leakage of periplasmic contents. In addition, the fusion proteins follow the outer membrane protein assembly pathway. This limits the maximum number of surface molecules and more importantly it is evident that completely folded proteins possessing disulphide bonds cannot be assembled across the outer membrane by this route (Klauser, T., et al. (1990) EMBO Journal. 9:1991–1999; Stathopoulos, C., et al. (1996) Applied Microbiology and Biotechnology. 45:112–119).

3.4. Extracellular Secretion.

There have been limited reports on extracellular secretion of unrelated proteins by some of the above mentioned secretion pathways. The Hly Type I secretion pathway has been adapted to delivery of heterologous antigens (Gentschev, I, et al. (1996) Gene 179:133–140). Although apparently successful, this system delivers proteins directly from the cytosol and would preclude any protein which require exposure to the periplasmic space for correct folding, e.g. disulphide bond formation.

It is summarised below some of the serious drawbacks associated with recombinant protein expression:

(i) Periplasmic expression systems: Many heterologous polypeptides expressed in *E. coli* are either degraded or form aggregates and inclusion bodies as a result of incorrect folding. This may occur despite targeting of the protein to a preferred location, i.e. the cytosol (with a more reducing environment) or the periplasm (with a more oxidising environment and specific chaperones involved in folding). Employment of a signal sequence to proteins targeted to the periplasm results in varying degrees of efficiency of precursor processing, completion of translocation and correct folding. Some incorrectly folded proteins remain associated with the inner membrane and induce toxicity. In addition, they are extensively degraded resulting in a poor yield. Others accumulate in a non-native conformation as insoluble aggregates. Systems employing fusion proteins are available. These may to some degree enhance solubility of some recombinant proteins but others remain insoluble due to incomplete folding of the heterologous domain. A system leading to stimulation of the early folding event following translocation across the inner membrane would clearly enable periplasmic expression of many heterologous polypeptides which have thus far eluded successful expression in *E. coli.*

(ii) Surface localisation in Gram negative bacteria: Generally, there is a strict limitation in the size of epitopes which can be expressed at the cell surface using proven surface expression vectors. Systems that permit surface expression of whole domains or proteins by fusion them to an outer membrane protein lead to membrane permeabilisation, periplasmic leakage and toxicity. In addition, there are limitations on the extent to which proteins can be folded if they are to be exported by this pathway. Finally, as these systems all use integral membrane proteins, they are limited with respect to the maximum expression level and would be very laborious to purify.

SUMMARY OF THE INVENTION

The present invention provides bacterial strains for secretion of soluble biologically active recombinant heterologous proteins into periplasm or on a surface/into a cultivation medium of bacteria. The invention exploits the secretion system of Gram-negative bacteria including periplasmic chaperones and usher/secretin proteins. For accomplishing the aim, the bacterial strains simultaneously express the fusion protein (signal peptide)-(mature heterologous protein)-(subunit of a bacterial surface structure, Caf1), periplasmic chaperone specific for the subunit, and outer membrane usher/secretin protein specific for the subunit. Secretion of fusion proteins: (signal peptide of Caf1)-(mature human IL-1β)-(mature Caf1), (signal peptide of Caf1)-(mature human GM-CSF)-(mature Caf1), and (signal peptide of Caf1)-(mature human IL-1ra)-(mature Caf1) that were expressed in *Escherichia coli* simultaneously with the periplasmic chaperone Caf1M and the usher/secretin protein Caf1A are examples of the use of the invention.

BRIEF DESCRIPTION OF THE DRAWINGS

FIG. 7. The N-terminal sequence of mature CIC. After partial purification of periplasmic fractions on a DEAE-Sepharose CL-6B column (Pharmacia, Sweden) proteins were separated by SDS-PAGE followed by blotting onto a PVDF-membrane (Amersham, UK). The desired bands were excised and placed onto a polybrene coated and precycled glass fiber filter. Amino acid sequence analyses were performed with an Applied Biosystems model 477A protein sequencer equipped with on-line Applied Biosystems model 120A phenylthiohydantoin amino acid analyser.

DETAILED DESCRIPTION OF THE INVENTION

Figure 1:
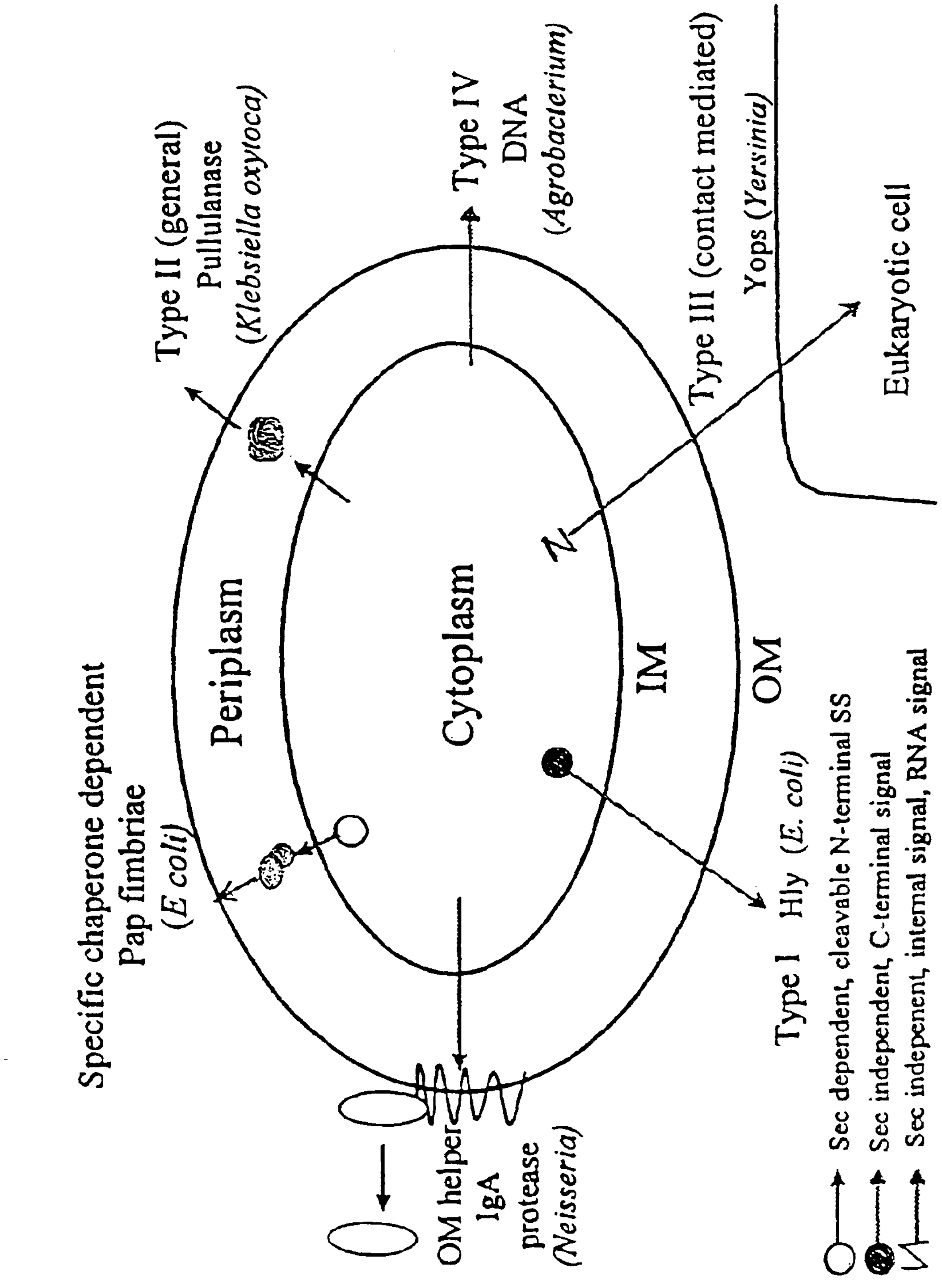
FIG. 1. Extracellular secretion systems in Gram negative bacteria. Major components include: (i) Type I (e.g. HlyA)–inner membrane (IM) ABC transporter (Hly B and D)+an outer membrane (OM) protein (Tol C), no periplasmic intermediate detected; (ii) Type II (e.g. pullulanase)–Sec system for translocation across IM; translocation across OM–14 pul gene products including an OM secretin (PulC , S), eight IM pul products (Pul C, E,F, K–O) and four prepilin-like products (Pul G–J), evidence supports periplasmic intermediate; (iii) Type II (e.g. Yops)–24 Ysc proteins including an OM secretin (YscC) and IM ATPase (YscN), specific Syc cytosolic chaperones, and Yop B and D required for delivery to eukaryotic cell (iv) Type IV—newly classified group including systems involved in DNA transfer to plant or other bacterial cells (e.g. T-DNA of *Agrobacterium tumefaciens*, 11 virB genes, unlikely to go via periplasmic intermediate) and pertussis toxin export (9 ptl genes, periplasmic assembly of toxin likely). (v) OM helper (e.g. IgA protease)—Sec system for translocation across IM; no specific accessory proteins; uses a 'helper domain' within the protein which presumably follows the OM protein assembly pathway and folds into the OM exposing the secreted domain on the surface; (vi) Specific chaperone mediated assembly (e.g.Pap pili)–Sec system for translocation across IM; translocation across OM–periplasmic chaperone (PapD) which specifically recognises pilin subunits, OM usher/secretin protein (PapC) homologous to PulC and YscC of TypeII and TypeIII pathways, respectively.

According to the present invention, secretion of proteins by gram-negative bacteria can be accomplished with adhesins via chaperone/usher pathway. The periplasmic chaperones of the system:

- mediate the partioning of nascently translocated subunits out of the inner membrane and into the periplasm;
- help in the folding of nascent subunits into a native conformation;
- protect the subunits from a proteolytic degradation.

The periplasm of wild type strains of bacteria contains oxidoreductases and additional chaperones (disulphide bond isomerase, DsbA and C, peptidyl prolyl cis-transisomerase, RotA, SurA and FkpA) which are essential to the correct folding of proteins.

The caf operon is the simplest operon in comparison to the size of the operons dedicated to most of the other extracellular secretion systems (Karlyshev, A. V. et al. (1994) in Biological Membranes: Structure, Biogenesis and Dynamic. NATO-ASI Series, vol. H-82, Op den Kamp, J. A. F., ed., pp. 321–330, Springer-Verlag, Berlin). It comprises of caf1R encoding a transcription regulator, the structural gene for the Caf1 polypeptide (Galyov, E. E. et al. (1990) FEBS Lett. 277, 230–232) and two genes encoding products for specific secretion of Caf1—the Caf1M periplasmic chaperone (Galyov, E. E. et al. (1991) FEBS Lett. 286.79–82) and Caf1A outer membrane protein (Karlyshev, A. V. et al. (1992) FEBS Lett. 297, 77–80).

Cal1 polypeptide is synthesised with a 20 aa cleavable SP. Following translocation across the inner membrane (presumably via the sec pathway), Caf1M binds to mature Caf1 and protects it from proteolytic degradation by assisting its folding and also its release from the inner membrane (Zav'yalov, V. et al. (1997) Biochem. J., 324, 571–578; Chapman D. et al. (1999) J. Bacteriology, in press). Interaction of subunit with Caf1M chaperone then stimulates a signal for interaction with the OM protein Caf1A and Caf1A translocates Caf1 to the cell surface. Surface assembled Caf1 forms an amorphous capsule-like structure on the surface of the bacteria. This surface structure can be readily recovered with the bacterial cells and washed off the surface to give a relatively pure preparation of the Caf1 protein. Caf1M chaperone and Caf1A usher are specific for Caf1 subunit and not suitable for a secretion of heterologous proteins from this point of view. However, surprisingly it was found in the present invention that the fusions of three different heterologous proteins with the Caf1 subunit are secreted in soluble biologically active form and protected from proteolytic degradation when expressed simultaneously with the Caf1M chaperone.

According to the present invention Caf system can be applied for:

- production of recombinant heterologous proteins in the periplasm of bacteria in a soluble, biologically active conformation;
- surface display of whole recombinant heterologous proteins on Gram-negative bacteria—for obtaining heterologous live attenuated vaccines, construction whole cell ligands, whole cell biocatalysts, purificaton of recombinant heterologous protein from cell surface by washing fusion protein out of the cell surface, or by proteolytic cleavage of fusion protein;
- surface display of heterologous amino acid sequences (epitopes) within Caf1 subunit, and use as ligand, vaccine candidate etc.

Potential Applications of the Caf System:

1. Caf1SP-export across the IM: As with many other secretory proteins the Caf1 signal sequence can be used directly for secretion of proteins across the bacterial inner membrane. It contains no positively charged residues at its C-terminus that might interfere with export and can therefore be used directly. As the secreted protein would follow the Sec pathway to the periplasm, the efficiency of export of the heterologous protein would also depend on the nature of the protein to be secreted. In particular, efficiency of secretion would depend on the N-terminus of the mature polypeptide, absence of long potential anchor sequences within the secreted protein, and absence of protein folding prior to export. The first two features can be addressed by altering the relevant sequences. 'Premature' folding is more difficult to control although excess of cytosolic SecB, GroEL, DnaK chaperone may delay folding in some instances. Following translocation across the IM and SP cleavage, release of the heterologous protein from the IM and folding of the protein would again be dependent on the nature of the heterologous protein itself.
2. Caf1M chaperoning in the periplasm: The caf system has the added advantage that it includes a periplasmic chaperone which specifically binds to the Caf1 subunit. Caf1M prevents degradation of the Caf1 subunit, probably via enhanced folding and release from the IM. Chaperone recognition is via the C-terminus of the Caf1 subunit although interaction with other parts of the Caf1 subunit may also be required for high affinity binding. Hence, fusion of the Caf1 subunit C-terminally to the protein destined for release may stimulate folding of the heterologous protein, aid release of the protein from the IM, increase its solubility and prevent aggregation (formation of periplasmic inclusion bodies) and proteolytic degradation.
3. Caf1A—export of heterologous proteins extracellularly across the outer membrane. Caf1M chaperone also targets Caf1 to the OM secretin Caf1A. Following interaction of the complex with Caf1A secretin, the Caf1 is translocated across the outer membrane and forms a large polymeric structure on the cell surface-anchored via Caf1A. For the case that the anchoring is disfavored a proper mutant of Caf1 can be prepared. Thus, inclusion of Caf1A in the expression vector would permit targeting of the recombinant protein to the Caf1A secretin.

4. Hybrid proteins exported by this system could be proteolytically cleaved to remove Caf1 by introduction of an appropriate cleavage site between Caf1 and the protein of interest. For proteins arrayed on the cell surface of *E. coli* this provides an enormously efficient method of purification from isolated cells. Cell surface localised hybrid could also be used for vaccine preparation, ligand binding or as whole cell biocatalyst. Proteins secreted from the cell or recovered from the periplasm would be already in a highly purified form. All proteins secreted by this system would be exposed to the periplasm, offering the milieu for correct folding of secreted proteins. Using this system, the probability of folding into a functional protein/domain would be further increased for some fusion proteins due to interaction with the Caf1M chaperone.

In addition to secretion of whole proteins or domains as an N-terminal fusion to the Caf1 subunit (or possibly smaller domain thereof), it will undoubtedly also prove to be the case that short epitopes can be inserted into permissive sites within the Caf1 subunit permitting surface display of epitopes. Similarly, short peptides can be inserted into the FGL site of the Caf1M chaperone.

Summary of Potential Advantages of the Caf System as Applied to Heterologous Secretion n Gram Negative Bacteria:

- despite the fact that protein hIL-1β is insoluble in the periplasm and a fusion hIL-1β-Caf1 is also insoluble, co-expression with the Caf1M chaperone surprisingly led to a soluble product. Hence, the Caf1M chaperone catalyses folding, not only of the carrier Caf1 domain, but also of the IL-1β domain, resulting in release from the membrane and formation of a processed, soluble product. Because of correct folding the heterologous fusion protein is not degraded and accumulates in high levels. I.e. Caf1M can stimulate folding, membrane release and solubility of heterologous polypeptides expressed as Caf1 fusion proteins:
- while available systems of surface display of whole proteins in *E. coli* result in problems of loss of integrity of the outer membrane and have limitations as to the extent of folding of the exported protein, the caf system has not these limitations. The fusion protein is anchored to the cell surface or released as a soluble protein without disrupting the membrane. Similarly, assembly does not follow the folding pathway of outer membrane proteins and a fully folded fusion protein is exported;
- option to readily express high levels of recombinant protein in periplasm (Caf1M alone) or cell surface/media (Caf1M+Caf1) using the same system;
- ready purification from the cell surface by proteolytic cleavage or recovery in high levels from periplasmic fractions (whichever preferred);
- exquisitely simple compared to other potential extracellular secretion vectors-employing only a periplasmic chaperone (Caf1M) and outer membrane protein (Caf1A);
- ability to secrete extracellularly a whole protein or part thereof
- transient or permanent periplasmic localisation of fusion protein permits correct folding and oxidation of secretory proteins.

The invention is further illustrated here below with specific non-limiting examples. The examples describe the secretion of the fusion proteins (signal peptide of Caf1)-(mature human IL-1β)-(mature Caf1), (signal peptide of Caf1)-(mature GM-CSF)-(mature human Caf1) and (signal peptide of Caf1)-(mature human IL-1ra)-(mature Caf1) expressed in *Escherichia coli* simultaneously with the periplasmic chaperone Caf1M and the usher/secretin protein Caf1A as the examples of the use of the system. Even though Examples describe secretion of 3 proteins it is obvious that any other protein can be secreted using this system. In addition, although *E. coli* is used as the host microbe containing the expression system in these examples, it is obvious that also other cells having proper periplasmic space for accommodating the caf expression system can be used.

EXAMPLE I

Fusion or hIL-1β with the Signal Peptide of the Caf1 Protein

The Caf1 signal peptide ($^{s.p.}$Caf1) was fused with hIL-1β in three variants (FIG. 2). 1. $^{s.p.}$Caf1-hIL-1β was the straight fusion where the last amino acid of the Caf1 signal peptide was joint to the first amino acid of hIL-1β. 2. $^{s.p.}$Caf1(−2)-hIL-1β was the straight fusion with a mutation in the Caf1 signal peptide Asn(−2)Asp. 3. $^{s.p.}$Caf1(+3)hIL-1β was the fusion containing in the joint region three N-terminal amino acids from mature Caf1 to preserve the natural processing site.

Here and thereafter DNA manipulations and transformation of *E. coli* were accomplished according to Maniatis, T., et al. (1989) Molecular Cloning: A Laboratory Manual, 2nd edn., Cold Spring Harbor Laboratory Press, Cold Spring Harbor. Restriction enzymes, mung-bean nuclease, and T4 DNA ligase were purchased from Promega (USA). Taq DNA polymerase (Hytest, Finland) was used for polymerase chain reaction (PCR) experiments. Nucleotide sequencing was carried out using the TaqTrack sequencing kit (Promega, USA). Elution of DNA fragments from agarose gels was performed with the USBClean kit (USB, USA). The following oligonucleotides were used in EXAMPLES 1 and 2 (SEQ ID NOS: 1–13):

CAF-RI 5'-GGGAATTCAGAGGTAATATATGAAAAAAATC-3'

IL-PST 5'-CCGCCTGCAGATGCGGCACCTGTACGATCACTG-3'

CAF-PST 5'-CCGCCTGCAGTTGCAATAGTTCCAAATA-3'

IL-Primer 5'-AGAACACCACTTGTTGCTCC-3'

Blunt 5'-TGGAACTATFGCAACTGCAAATGCGGCACCTGTACGA-3'

3AA 5'-GCAACTGCAAATGCGGCAGATTTAGCACCTGTACGATC-ACTG-3'

IL-BamHI 5'-ACCGGATCCACCTCCACCAGATCCACCTCCGGAAGACACA AATTGCATGG-3'

BamHI-5'-GGTGGATCCGGTGGTGGTGGATCTGCA-GAJTTAACTGCA

Caf AGCAC-3'

Caf-SalI 5'-GCCAAGCTTGTCGACGAGGGTTAGGCTCAAAGT-3'

SBEKP-1 5'-TCGACAGATCTCGAATTCCGGTACCGGCTGCA-3'

SBEKP-2 3'-GTCTAGAGCTTAAGGCCATGGCCG-5'
STOP 5'-GATCATTAATTAAT-3'
TRC 5'-CCAGATCTGGCAAATATTCTGAAATG-3'

Figure 2:
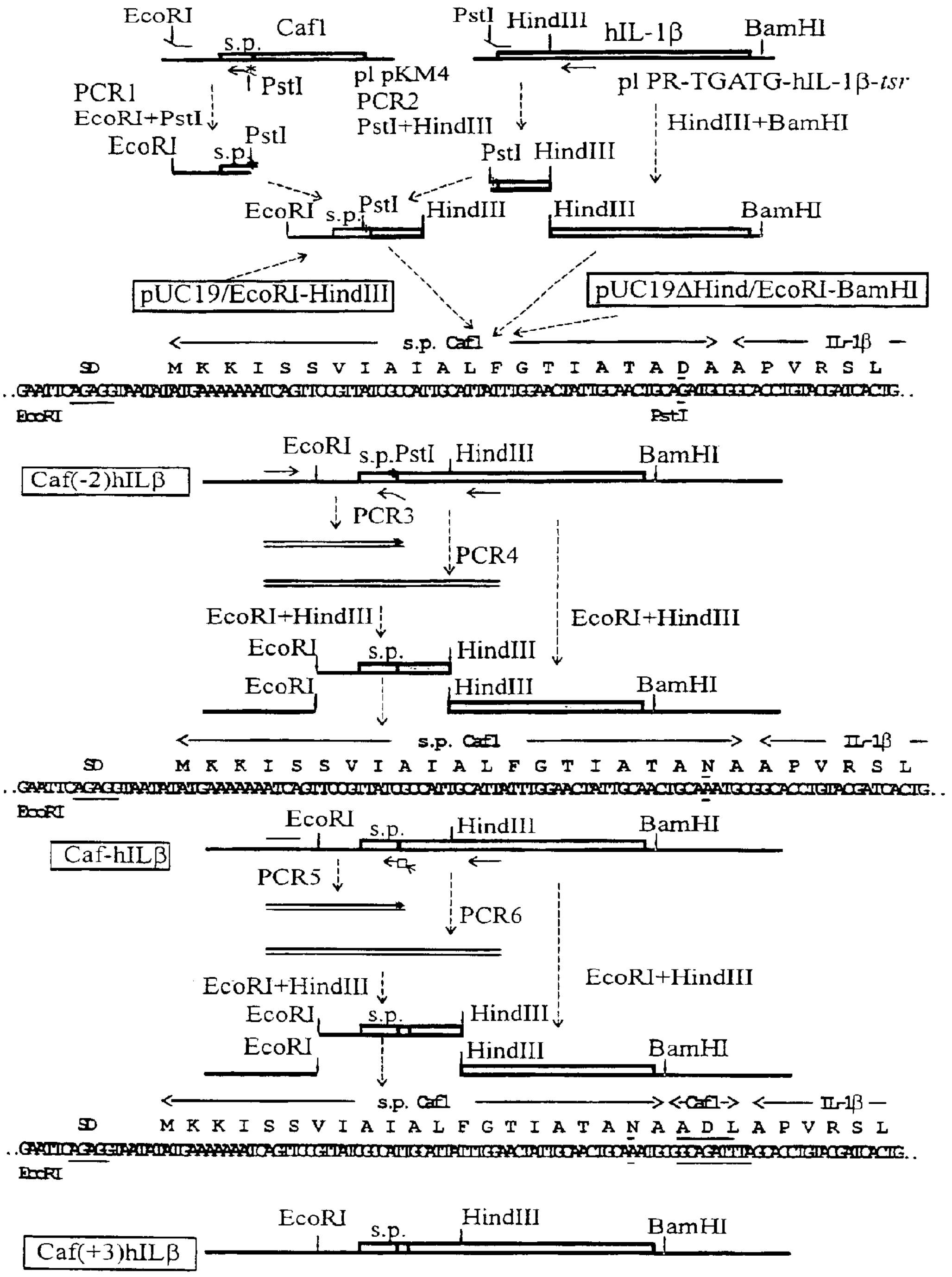
FIG. 2. Construction of hybrid genes coding for $^{s.p.}$Caf1-hIL-1β fusion proteins (SEQ ID NOS: 20–25).

The genetic constructs coding three fusion proteins $^{s.p.}$Caf1-hIL-1β were made according to the scheme in FIG. 2. The EcoRI-PstI fragment (about 110 bp) coding the Caf1 5'-untranslated region and N-terminal part of Caf1 signal peptide with the mutation Asn(−2)Asp was obtains by PCR using CAF-RI and IL-Pst oligonucleotides and the template plasmid pKM4 (Karlyshev, A. V., et at. (1992) FEBS Letters 297, 77–80) followed by digestion of PCR1 product with EcoRI and PsI. The PstI-HindIII fragment coding for the C-terminal part of Caf1 signal peptide joint to the N-terminus of hIL-β was obtained by PCR where CAF-PST and IL-Primer oligonucleotides and the template plasmid pPR-TGATG-hIL-1β-tsr (Mashko, S. V., et al. (1991) Gene 97, 259–266) were used. The PCR2 product was digested with PstI and HindIII. The two fragments were ligated together with a vector fragment pUC19/EcoRI-HindIII. The nucleotide structure of the resulted EcoRI-HindIII insert was verified by DNA sequencing. The EcoRI-HindIII fragment obtained as described and the HindIII-BamHI fragment isolated from pPR-TGATG-hIL-1β-tsr were ligated together with the EcoRI-BamHI vector fragment of pUCΔ19 ΔHindIII (a derivative of pUC19 where the HindIII site was deleted by filling of sticky ends followed ban blunt-end ligation). The EcoRI-BamHI fragment thus obtained encoded the $^{s.p.}$Caf1(−2)hIL-β fusion protein. The point mutation G to A converting the $^{s.p.}$Caf1(−2)hIL-1β gene into the Caf1-hIL-1β gene was made by means of two-step PCR procedure (Landt, O., Grunert. H.-P. and Hahn, U. (1990) Gene 96, 125–128) using the BLUNT oligonucleotide and two flanking primers (M13 Sequence Primer and IL-Primer) with pUC19ΔHindIII/$^{s.p.}$Caf1(−2)hIL-1β plasmid as a template. In the first step, an intermediate PCR product was obtained from the mutagenic BLUNT oligonucleotide and the M13 Sequence Primer. After purification from an agarose gel, the intermediate PCR product was used with the IL-Primer in the second PCR step. The latter PCR product was digested with EcoRI and HindIII followed by ligation into the vector fragment made by restriction of the pUC19ΔHindIII/$^{s.p.}$Caf1(−2)hIL-1β plasmid with the same enzymes. Thus, the EcoRI-HindIII fragment providing the Asn(−2)Asp mutation in the $^{s.p.}$Caf1(−2)hIL-1β fusion protein was replaced by the corresponding fragment coding the natural Caf1 signal peptide, and the $^{s.p.}$Caf1-hIL-1β gene was obtained. The $^{s.p.}$Caf1(+3)hIL-1β gene was constructed in a similar way using the 3AA oligonucleotide as a mutagenic primer and pUC19ΔHindIII/$^{s.p.}$Caf1-hIL-β plasmid as a template. In all three hybrid genes the EcoRI-HindIII fragments were sequenced to prove correct nucleotide structures.

EcoRI-BamHI fragments coding for the fusion proteins were excised from plasmids described above and were transferred into pKKmod (a derivative of pKK 223-3 (Pharmacia) created by deletion of BamHI- and SalI-sites in the tet gene region and by replacement of the pKK 223-3 polylinker with the pUC18 polylinker). The expression plasmids pKKmod/$^{s.p.}$Caf1(−2)hIL-1β, pKKmod/$^{s.p.}$Caf1-hIL-1β and pKKmod/$^{s.p.}$Caf1(+3)hIL-1β were thus obtained, and *E. coli* JM105 [F' traD36, lacI$^9$Δ(lacZ)M15, proA$^+$B$^+$/thi. rpsL(Str$^+$), endA. sbcB. sbcC, hsdR4($r_k^-m_k^+$), Δ(lac-proAB)] (NE BioLabs) were transformed with these plasmids.

Expression and processing of $^{s.p.}$Caf1-hIL-1β, $^{s.p.}$Caf1(−2)hIL-β, and $^{s.p.}$Caf1(+3)hIL-1β fusion proteins were monitored by SDS-PAGE electrophoresis and immunoblotting. The recombinant *E. coli* strains were grown to about 0.5 AU at 600 nm, IPTG (0.5 mM) was added and cells were grown further. Soluble and insoluble proteins were analysed as separate fractions obtained as follows. After certain time intervals, samples of the growth culture with fixed amount of cells were withdrawn cells were precipitated and washed in 25 mM Tris-Cl, pH 7.5/100 mM NaCl/1 mM EDTA. Reprecipitated cells were suspended in 50 mM $H_3PO_4$-Tris, pH 6.8 and sonicated using Labsonic U Generator (B. Braun Diessel Biotech). The sonicated samples were centrifuged at 14,000 g for 10 min. Supernatant contained soluble proteins. Insoluble proteins were extracted from the pellet with the SDS-PAGE sample buffer containing 2% SDS and 5% β-mercaptoethanol.

Here and thereafter 10–15% SDS-PAGE of the proteins from both soluble and insoluble fractions was performed according to the Laemmli procedure in Mini-PROTEAN II apparatus (BIO-RAD). Proteins were transferred to a Hybond-C membrane (Amersham) by electroblotting in mini-Trans-Blot Electrophoretic Transfer Cell (BIO-RAD) followed by immunodetection. Results of immunoblots were revealed with the ECL kit (Amersham). Polyclonal rabbit antibodies to hIL-1β (Calbiochem) and monospecific antibodies to Caf1 were used for visualisation of IL-1β and Caf1-containing fusion proteins. Rabbit polyclonal antibodies to Caf1M and mouse policlonal antibodies to Caf1A were used for detection Caf1M and Caf1A, correspondingly. The binding of the primary antibodies were visualised by rabbit (Calbiochem) and mouse (Amersham) conjugate.

Figure 3A:
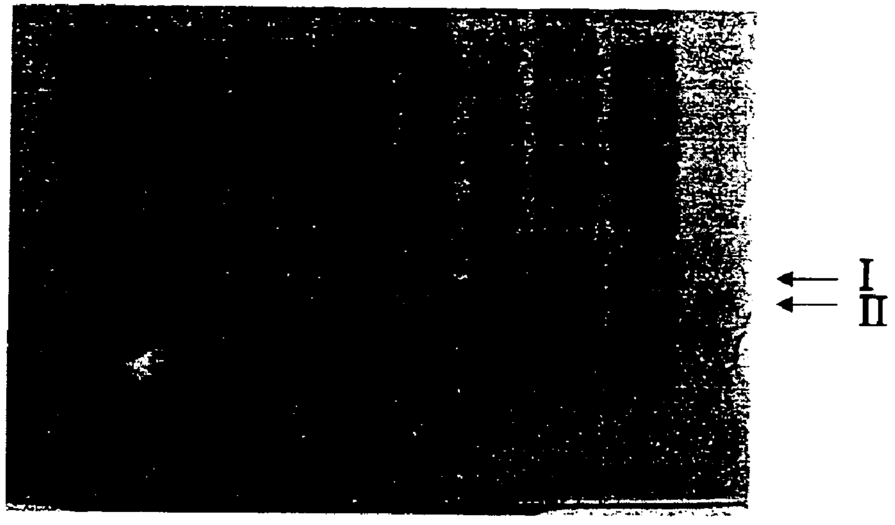
FIG. 3. Expression of $^{s.p.}$Caf1-hIL-1β fusion proteins. A. Coomassie Blue-stained SDS-PAGE of soluble (lanes 2–5) and insoluble (lanes 6–9) proteins from *E. coli* cells transformed with pKKmod (lanes 2, 6), pKKmod/$^{s.p.}$Caf1-hIL-1β (lanes 3, 7), pKKmod/$^{s.p.}$Caf1(−2)hIL-1β (lanes 4, 8), and pKKmod/$^{s.p.}$Caf1(+3)hIL-1β (lanes 5, 9). hIL-1β was loaded as a control (lanes 1, 10). B. Immunoblot of the same gel analysed with anti-hIL-1β rabbit polyclonal antibodies. Positions of unprocessed (I) and processed (II) hIL-1β are shown by arrows.

High expression was observed for all three fusion proteins (about 20–30% of total cell protein). However, in all three recombinant strains fractions of soluble proteins did not contain significant amounts of recombinant proteins (FIG. 3A and B, lanes 1–4). The recombinant hIL-1β protein was discovered in fractions of insoluble cell proteins (FIG. 3A and B, lanes 6–9). An additional hIL-β containing protein was clearly seen in all three constructs. Most probably, it was a product of rather specific proteolysis of unprocessed fusion protein accumulated in cytoplasm.

The straight fusion appeared not to be processed (FIG. 3A and B, lanes 7), while in the other two products the removal of Caf1 signal peptides from hIL-1β moieties achieved considerable levels (FIG. 3A and B, lanes 8,9).

To elucidate secretion of processed recombinant hIL-1β proteins, periplasmic proteins were separated from cytoplasmic proteins by osmotic shock procedure as follows. Cells precipitated from 10 ml of growth medium were suspended in 200 μl 20% (w/v) sucrose/0.3 M Tris-HCl, pH 8.0/0.5 MM EDTA and kept at room temperature for 10 min. Sucrose-treated cells obtained by centrifugation were suspended in ice-cold 10 MM $MgCl_2$/0.1 mM PMSF and incubated in ice water for 10 min. After centrifugation, periplasmic proteins were recovered in supernatant fractions. The pellets were suspended in 50 mM $H_3PO_4$-Tris, pH 6.8 and sonicated followed by centrifugation at 14,000 g for 10 min. These supernatants contained soluble cytoplasmic proteins. The activity of the cytoplasmic enzyme, glucose 6-phosphate dehydrogenase, was checked as a control of the purity of the periplasmic fraction (Naglak T. J. et al. 1990, 12, 603–611). The obtained samples of the periplasm fraction did not show more than 0.25% of the cytoplasmic glucose 6-phosphate dehydrogenase activity.

Figure 4A:
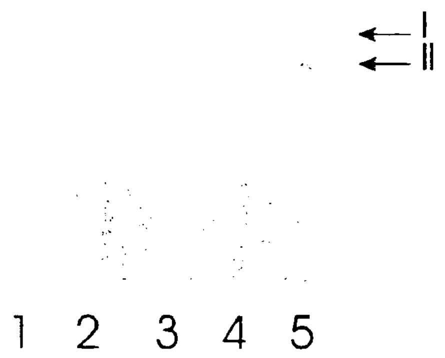
FIG. 4. Secretion of $^{s.p.}$Caf1-hIL-1β fusion proteins. Immunoblots of periplasmic (A) and soluble cytoplasmic (13) proteins from $^{s.p.}$Caf1(+3)hIL-1β (lane 1), $^{s.p.}$Caf1(−2) hIL-1β (lane 2), and $^{s.p.}$Caf1-hIL-1β (lane 3) expression strains. Corresponding proteins from cells harbouring pKK-mod were used for comparison (lane 4). hIL-1β was loaded as a control (lane 5). Proteins were analysed with anti-hIL-1β rabbit polyclonal antibodies. Positions of unprocessed (I) and processed (II) hIL-1β are shown by arrows.
Figure 4B:
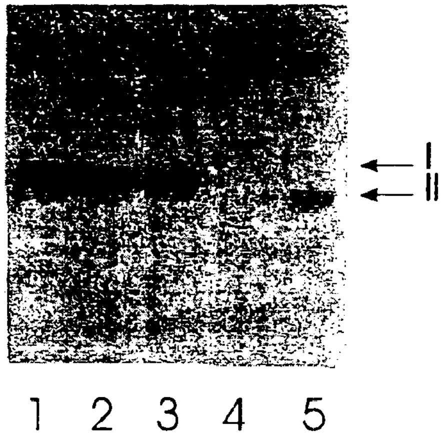

Western blot analysis of periplasmic and soluble cytoplasmic proteins (FIG. 4) has shown that only minor parts of the processed fusion proteins were found in a soluble form in periplasms of $^{s.p.}$Caf1(−2)hIL-β and $^{s.p.}$Caf1(+3)hIL-1β expression strains (FIG. 4A, lanes 1,2). No processed protein was detected in periplasm of ${}^{s.p.}$Caf1-hIL-1β expression strain (FIG. 4A, lane 3). Processed hIL-1β proteins were absent in cytoplasmic fractions (FIG. 4B).

Figure 5:
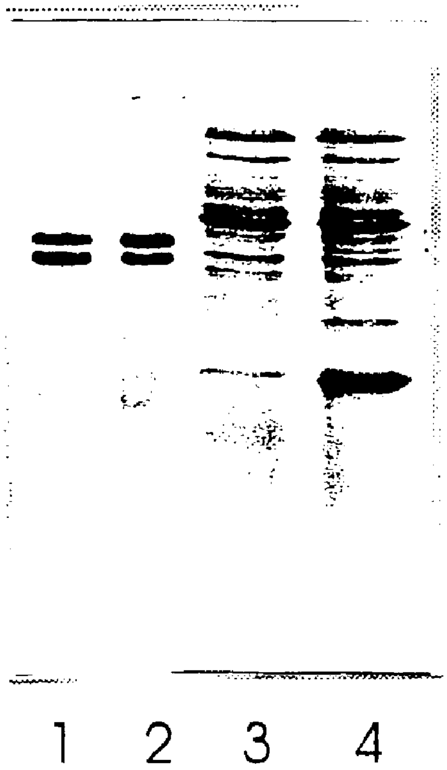
FIG. 5. Trypsin digestion of permeabilized cells. Insoluble proteins (lane 1–2) and soluble proteins (lane 3–4) were obtained from $^{s.p.}$Caf1(−2)hIL-1β expression cells before (lane 1,3) and after (lane 2,4) trypsin treatment.

The data obtained demonstrated that the ${}^{s.p.}$Caf1(−2)hIL-1β and ${}^{s.p.}$Caf1(+3)hIL-1β fusion proteins were partly processed (in contrast to the Caf1-hIL-1β fusion protein). Processed products were secreted into periplasm. However, the majority of the processed recombinant hIL-1β, accumulated in an insoluble form. Moreover, this insoluble protein is hidden from liquid phase of the periplasm since it is not digested during trypsin treatment of permeabilized cells (FIG. 5). Variation of growth temperature and concentration of the inductor did not facilitate the Caf1 signal peptide removal and secretion of hIL-1β (data not shown).

EXAMPLE 2

Fusion of ${}^{s.p.}$Caf1(−2)hIL-β with the Caf1 Protein Sequence and Expression of Fused Protein in the Presence of Chaperone and Usher Proteins The CIC (${}^{s.p.}$Caf-IL-1β-Caf) protein was designed where the ${}^{s.p.}$Caf1(−2)hIL-1β amino acid sequence (N-terminus of the fusion) was linked to the Caf1 protein sequence (C-terminus of the fusion) through a spacer GlyGlyGlyGly-Ser repeated three times. The spacer was inserted to minimise possible conformational problems of the two proteins fused in CIC.

Figure 3B:
Figure 6:
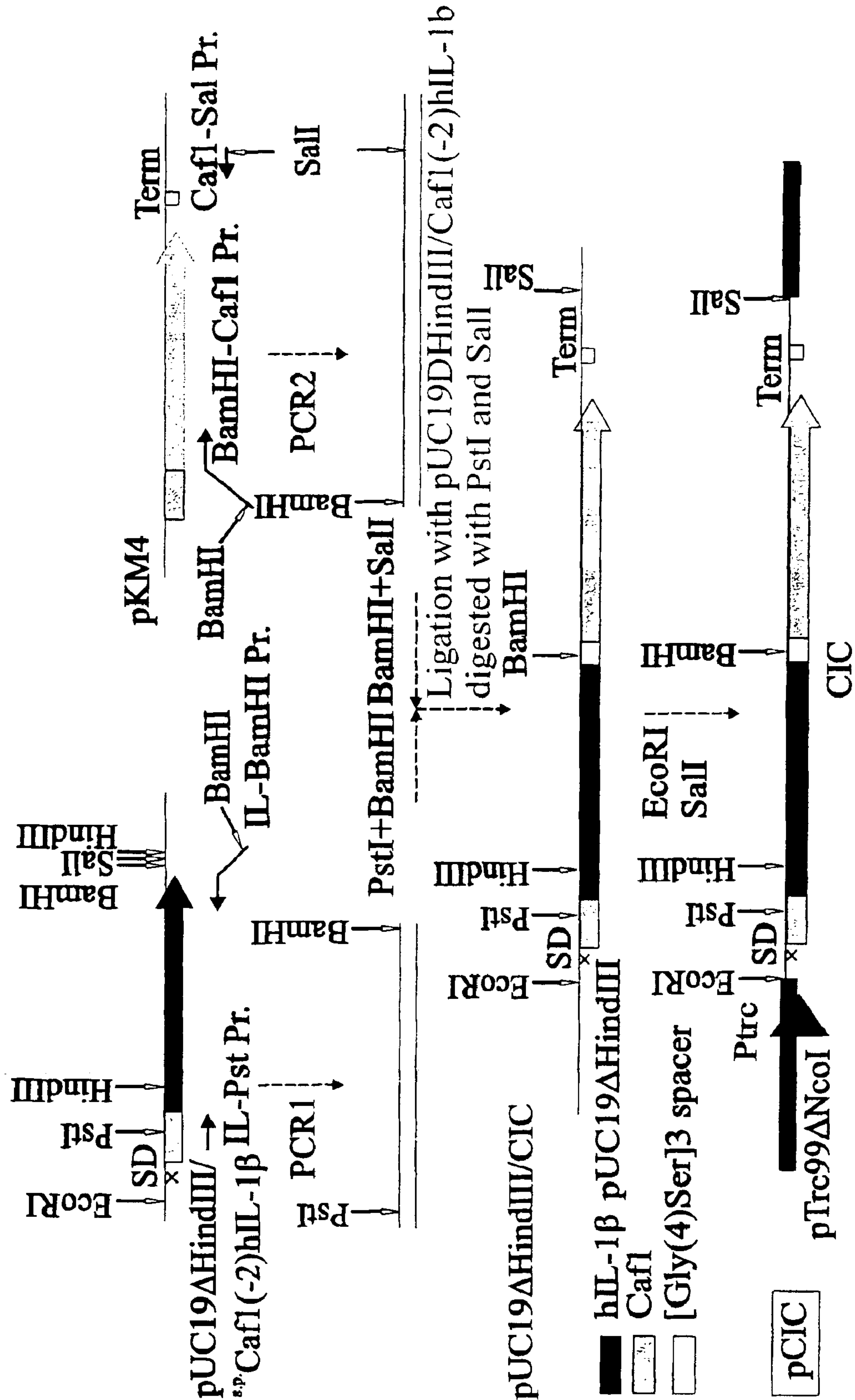
FIG. 6. Construction of pCIC plasmid coding for the $^{s.p.}$Caf1(−2)-hIL-1β-Caf1 fusion protein.

The pCIC expression vector was constructed according to the scheme on FIG. 6. The IL part of CIC was obtained by PCR using IL-Pst and IL-BamHI oligonucleotides as primers and the pUC19ΔHindIII/${}^{s.p.}$Caf1(−2)hIL-1β plasmid as a template. The Caf1 part of CIC was obtained by PCR using BamHI-Caf1 and Caf1-SalI oligonucleotides as promers and the pKM4 plasmid as a template. PCR products were digested with restrictases as shown in FIG. 3 followed by triple ligation with the pUC19ΔHindIII/${}^{s.p.}$Caf1(−2)hIL-β vector obtained by digestion with PstI and SalI. To produce pCIC, EcoRI-SalI fragment was excised from pUC19ΔHindIII/CIC plasmid and ligated into the EcoRI-SalI vector obtained from pTrc99ΔNco plasmid (a derivative of pTrc99a (Pharmacia) created by digestion with NcoI followed by mung-bean nuclease treatment and ligation of blunt ends).

Figure 7:
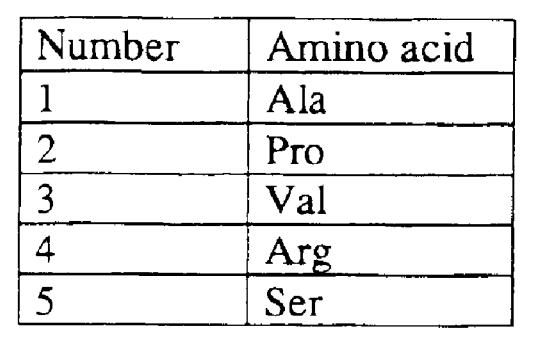
Figure 8A:
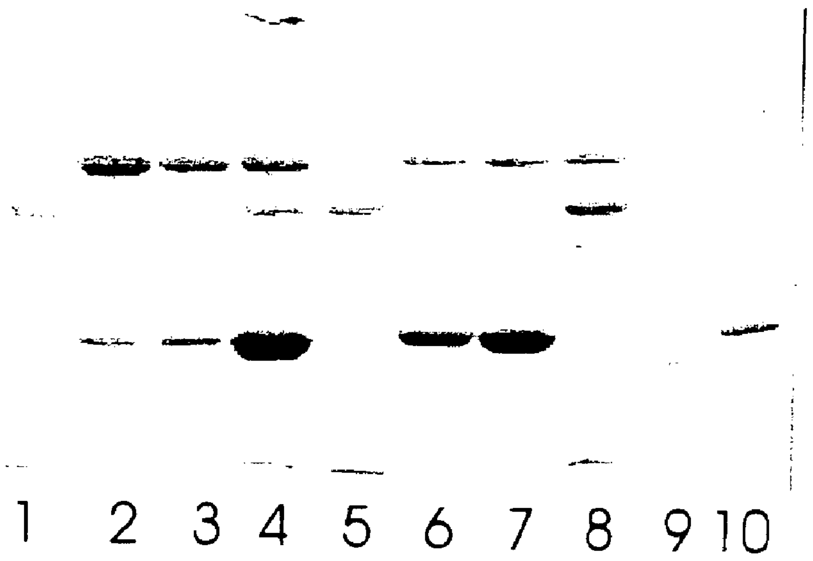
FIG. 8. Caf1M facilitates expression of $^{s.p.}$Caf1(−2)-hIL-1β-Caf1 (CIC). A. Coomassie Blue-stained SDS-PAGE of periplasmic fraction from cells transformed with: pCIC (lane 1), pFMA (lane 2), pMA-CIC (lane 3), pA-CIC (lane 4), pM-CIC (lane 5), pMA-PrCIC (lane 6), pA-PrCIC(lane 7), pM-PrCIC(lane 8), pCIC, pCaf1M (lane 9), pCIC, and pCaf1MA (lane 10). B. Immunoblot of the same gel analysed with anti-hIL-1β rabbit polyclonal antibodies.
Figure 8B:
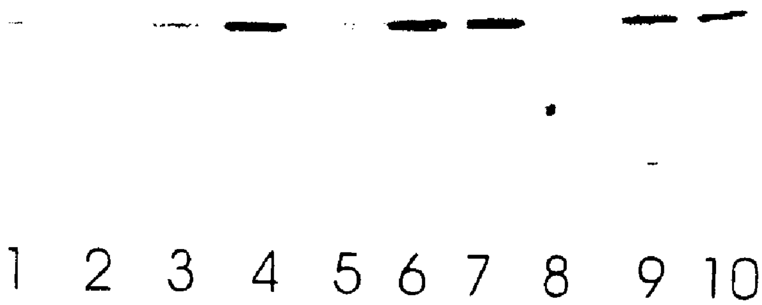

After IPTG induction. *E. coli* JM105 cells harbouring pCIC produced the CIC fusion protein that was successfully processed. A precise removal of the signal peptide was proved by N-terminal sequencing of the soluble periplasmic CIC (FIG. 7). However, only a minor part of the mature IL-1β-Caf1 protein was extracted by an osmotic shock procedure (FIG. 8B, lane 1). Main part of the protein was found in the membrane fraction (data not shown), similar to mature hIL-1β.

Expression/secretion of CIC in the presence of the chaperone (Caf1M) and the usher (Caf1A) was studied in two systems. a) caf1m and Caf1a genes were situated on a pACYC plasmid compatible with the pTrc99 derivative coding for CIC. b) caf1m, caf1a and cic genes together formed an artificial operon.

In compatible plasmid experiments, *E. coli* JM105 cells were transformed simultaneously with pCIC and pCaf1M (a plasmid carrying caf1m gene under tac promoter in a pACYC184 derivative, see EXAMPLE 3) to study influence of the chaperone on secretion of hIL-1β fusion protein. Further, pCaf1MA, a Caf1M-Caf1A expression/secretion plasmid, was created as follows. ApaLI-ApaLI fragment containing caf1m and caf1a genes under trc promoter was excised from the pFMA plasmid (Chapman D., et al. Structural and functional significance of the FGL sequence of the periplasmic chaperone, Caf1M, of *Yersinia pestis*" J. Bacteriology, in press) and ligated into the vector obtained by digestion of pCaf1M with ApaLI. *E. coli* JM105 cells were transformed simultaneously with pCIC and pCaf1MA to obtain co-expression of all three proteins.

Figure 9:
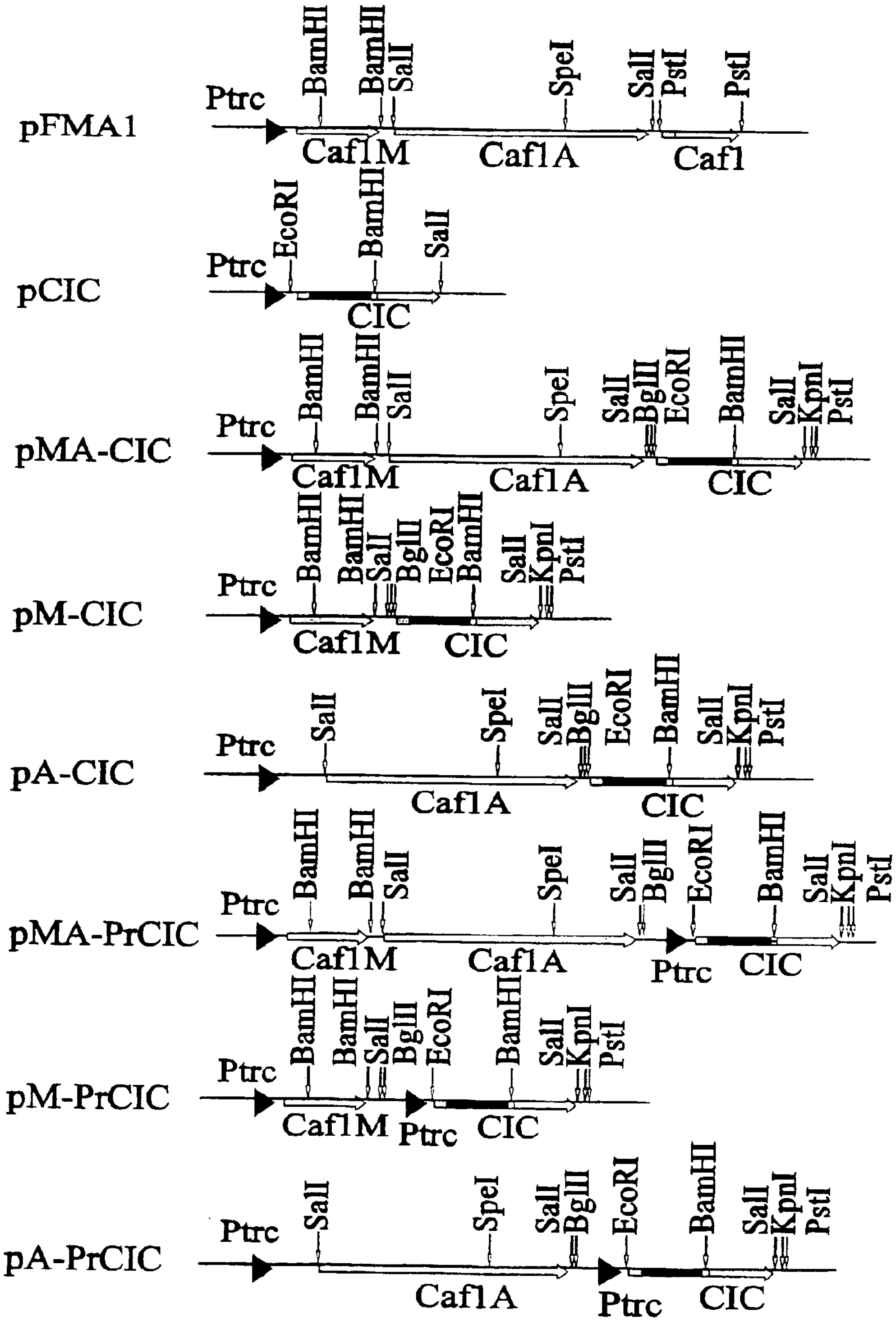
FIG. 9. Graphical representation of plasmids constructed for operon-like co-expression experiments with Caf1M, Caf1A, and CIC. pFMA and pCIC are given for comparison.

Several plasmids were constructed to study expression and secretion of CIC, Caf1M and Caf1A proteins produced from an artificial operon (FIG. 9). To replace the caf1 gene with a SBEKP synthetic polylinker, a pMA-link plasmid was obtained by triple ligation of a pFMA/PstI-SpeI vector, a SpeI-PstI fragment of pFMA, and SBEKP-1 and SBEKP-2 oligonucleotides annealed together. A plasmid pM-link was obtained from the pMA-link plasmid by excision of a SalI-SalI fragment coding for the Caf1A protein followed by self-ligation of the vector. A pA-link plasmid was obtained from the pMA-link plasmid by excision of a BamHI-BamHI fragment coding for the C-terminal part of Caf1M protein. To interrupt the Caf1M translation frame, the stop-codon was inserted by ligation of a self-complementary STOP oligonucleotide into the BamHI site. The insertion of the STOP oligonucleotide resulted in the loss of BamHI site. A fragment coding for the CIC protein was excised from pCIC with EcoRI and SalI, cloned in pBCSK$^{+}$ (Stratagene, USA), and recovered with EcoRI and KpnI. To obtain pMA-CIC, pM-CIC, and pA-CIC plasmids, the EcoRI-KpnI fragment was cloned into corresponding sites of pMA-link, pM-link, and pA-link. A plasmid pM-PrCIC differed from pM-CIC by the presence of additional trc-promoter before the CIC gene, and was obtained as follows. A DNA fragment coding for the trc-promoter and the 5'-region of the cic gene was obtained by PCR using TRC and CAF-Pst oligonucleotides as primers and pCIC as a template. The PCR product was digested with BglII and EcoRI followed by ligation of the BglII-EcoRI fragment coding for the trc-promoter into corresponding sites of pM-CIC, pMA-PrCIC and pA-PrCIC were obtained by ligation of the BglII-KpnI fragment from pM-PrCIC into corresponding sites of pMA-link and pA-link. *E. coli* NM522 [F', proAB, lacI$^{q}$Δ(lacZ)M15/supE, thi-I, Δ(lac-proAB), Δ(hsdSM-mcrB)5, ($r_k^- m_k^+$)] (Stratagene, USA) was used as a host strain for plasmids described here.

Similar results were obtained in both co-expression methods. Simultaneous expression of CIC and Caf1M significantly increased the concentration of the mature CIC in the periplasm. The results demonstrated that periplasmic molecular chaperone promoted a release of the secreted protein from the inner membrane as well as prevented protein from degradation and unspecific aggregation.

In the presence of Caf1M a significant part of the mature CIC protein was detected in a periplasmic fraction (FIG. 8B, lanes 3,4,6,7,9,10). Elevated amount of secreted and soluble CIC co-expressed with Caf1M demonstrates that the periplasmic molecular chaperone promotes a release of the secreted protein from an inner membrane. The critical role of the Caf1 part in the CIC protein in this promotion was proved in a similar experiment with a plasmid differed from pCIC by deletion of one base pair in the spacer. The deletion resulted in the frame shift of the Caf part of the fused gene. No facilitation of hIL-1β secretion was observed when cells harboured the mutated plasmid (data not shown).

Caf1M prevented CIC from degradation. As shown in FIG. 8B, lane 1, the mature CIC protein in the periplasmic fraction rapidly degraded into a truncated form with a molecular weight about 20–23 kDa. In the presence of Caf1M the truncated form disappeared (FIG. 8B, lanes 3,4,6,7,10). The amount of the degraded form correlated with the amount of Caf1M. For example, when Caf1M was expressed from pCaf1M at a low level the truncated form was found (FIG. 8B, lane 9). However, the Caf1M amount was sufficient to facilitate a release of the fusion protein from the membrane. The specific digestion of the mature CIC occurred at a site in the Caf1 part of the fusion protein since the truncated form was well detected by the IL antibodies but not detected by the Caf1 antibodies (data not shown). Most probably the cleavage was due to the action of protease DegP, which had been shown is induced by unfolded secreted capsular or pilus subunits and cleaves them (Soto, G. E., et al. (1998) EMBO J., 17, 6155–6167).

Figure 10:
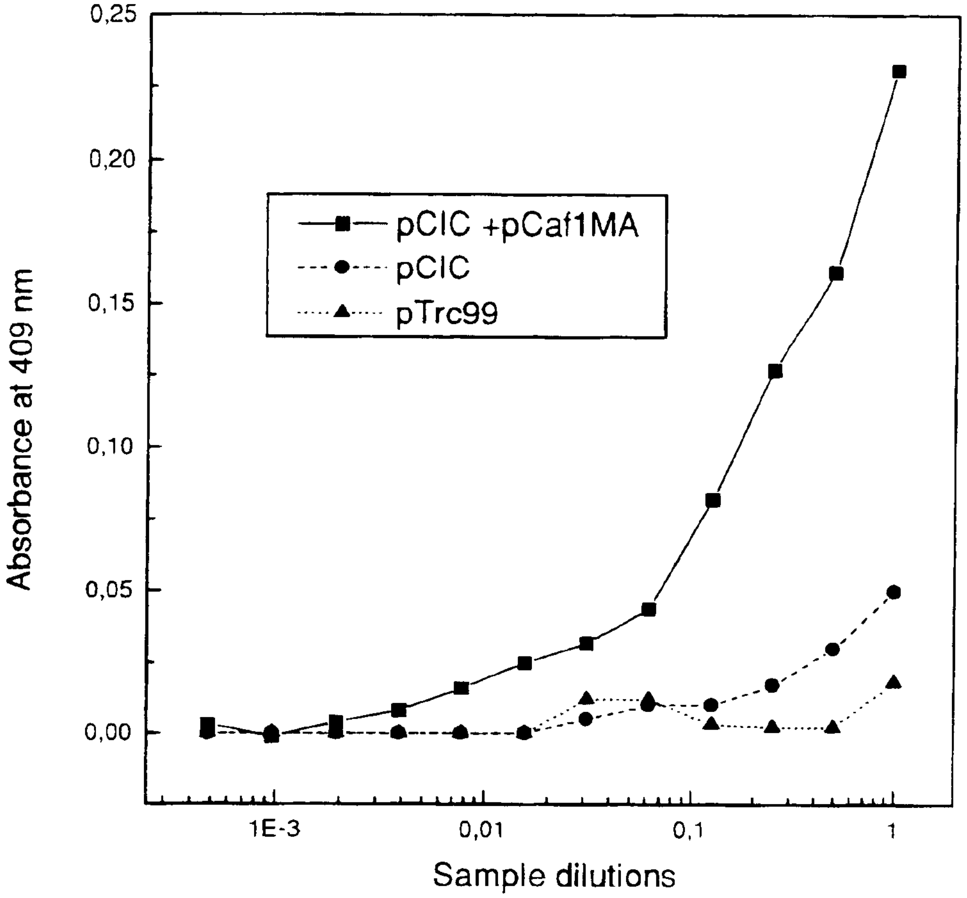
FIG. 10. Detection of CIC in periplasm with monoclonal anti-IL antibodies using ELISA. Detection of CIC in dilutions of a periplasm aliquot from control cells carrying pTrc99 with plasmid (triangles), from cells carrying pCIC (circles) and from cells carrying both pCIC and pCaf1MA (squares).

The hIL-1β part of CIC secreted in the presence of Caf1M was correctly folded. The mature CIC protein was detected with monoclonal antibodies to hIL-1β in ELISA (FIG. 10). ELISA was performed using monoclonal mouse antibodies to hIL-1β (HyTest, Finland) as it was described previously (Zav'yalov, V., et al. (1997) Biochem. J., 324, 571–578).

CIC was excreted onto a cell surface when expressed with both Caf1M and Caf1A. The presence of the molecular chaperone and the usher protein in cells transformed with pMA-CIC or with pCIC and pCaf1MA together was proved by immunoblotting with anti-Caf1M and anti-Caf1A antibodies (data not shown). To prove the excretion of CIC onto a cell surface, cell agglutination experiments were performed with reticulocyte monoclonal diagnosticum for detection of *Yersinia pestis* (Middle Asian Reaserch Institute, USSR). The *E. coli* cells expressed CIC, Caf1M, Caf1A were able to precipitate reticulocytes with surface bound monoclonal antibody to Caf1 at the concentration about $10^7$ cells/ml. Moreover, according to ELISA performed with anti-hIL-1β monoclonal antibodies, a small amount of hIL-1β was detected in cultural medium.

EXAMPLE 3

Co-expression of hGMCSF-Caf1 Fusion Protein and the Chaperone

The expression plasmid for the hGM-CSF-Caf1 fusion protein was based on pFGM13 described in: Petrovskaya L. E. et al. (1995) Russian Journal of Bio-organic Chemistry, 21, 785–791. The pFGM13 plasmid contained a synthetic gene coding for hGMCSF with Caf1 signal sequence (scaf1) cloned into HindIII and XbaI sites of pUC19. Transcription was controlled by the lac promoter and was inducible with IPTG. Translation of the scaf1-gmcsf gene in pFGM13 initiated at the first methionine codon of lacZ gene and utilises its Shine-Dalgarno sequence. A primary structure of the signal sequence (scaf1) encoded by this gene differed from wild-type one at its N-terminus, which contained seven extra residues from β-galactosidase N-terminus.

Figure 11:
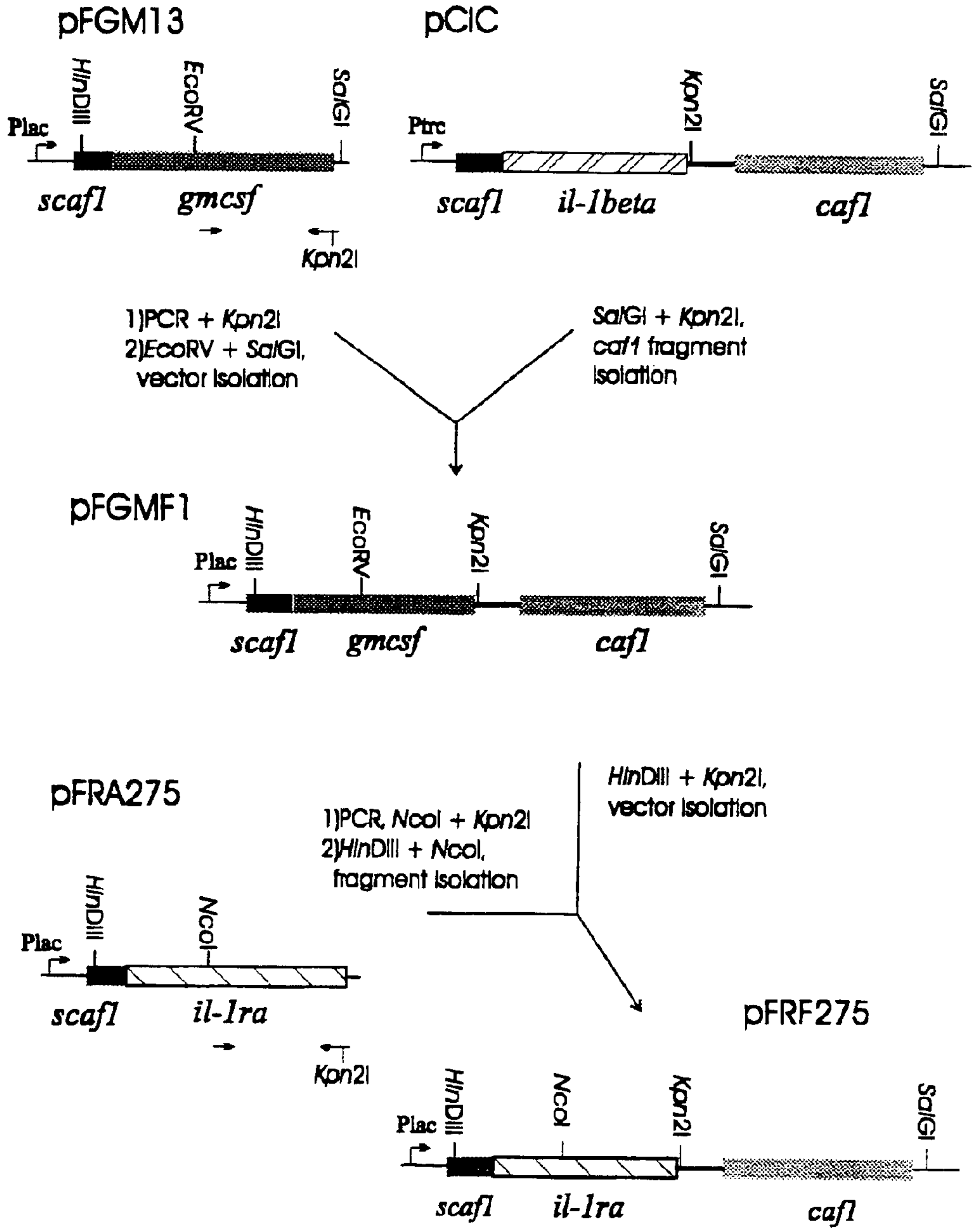
FIG. 11. Construction of pFGMF1 and pFRF275 plasmids coding for the scaf-GMCSF-Caf1 and scaf-IL1ra-Caf1fusion protein.

The construction of the pFGMF1 plasmid coding for the gmcsf-caf1 gene is shown in FIG. 11. The scaf1-gmcsf gene of pFGM13 was modified for the following cloning of the fragment from pCIC containing a spacer $(4GlySer)_3$ and the Caf1 coding region. The Kpn2I site was introduced at 3'-terminus of the gmcsf gene by PCR using two primers (5'ATCGGAAATGTTCGACCTTCAAG (SEQ ID NO: 14) and 5'ATTATTCCGGACTCCTGCACTGGTTCCCAGC) (SEQ ID NO: 15) and pFGM13 as a template. Pfu DNA Polymerase was used for a maximal fidelity. The PCR fragment was treated with Kpn2I followed by ligation into the EcoRV-SalGI large fragment of pFGM13 together with Kpn2I-SalGI fragment from pCIC. The final plasmid (pFGMF1) contained the gene encoding a hybrid precursor consisting of the scaf1 signal sequence, GMCSF with 2 N-terminal amino acid changes ($Ala_2Pro_3$ to Asp), a Ser $(4GlySer)_3$ spacer, and Caf1. The plasmid structure was confirmed by restriction analysis and sequencing of amplified regions.

Expression of the hybrid precursor gene in JM101 *E. coli* cells harbouring pFGMF1 was induced with 0.2 mM IPTG after cell culture reached an optical density 0,5–0.8. The growth with IPTG continued for 3 I Cells from 1 ml were collected by centrifugation and the pellet (total cell protein sample) was analysed by SDS-PAGE electrophoresis. A fraction of periplasmic proteins was isolated by the cold osmotic shock procedure (see EXAMPLE 1) from the cell pellet obtained from the rest of the culture.

Figure 12:
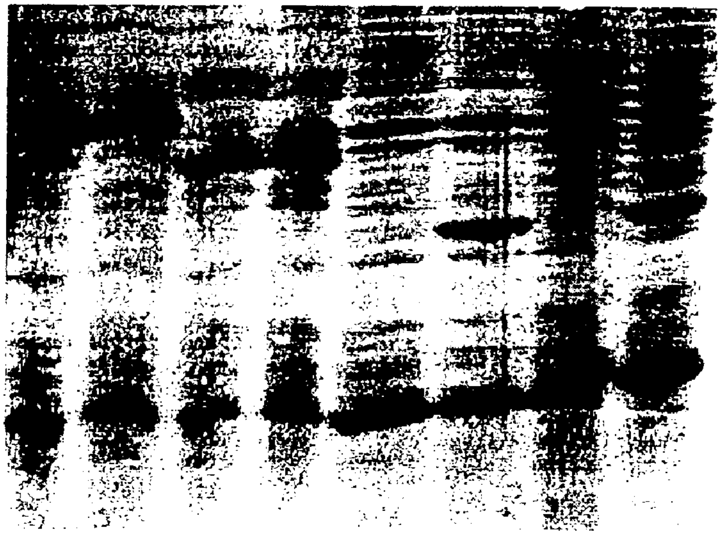
FIG. 12. Fractionation of proteins expressed in JM101 cells with plasmids pFGMF1 (lanes 3,4,7,8), pFRF275 (lanes 1,2,5,6), and pCaf1M (lanes 2,4,6,8). After induction cells were precipitated, resuspended in buffer with lysozyme and incubated on ice for 1 hour followed by sonication for 1 min. Soluble and insoluble proteins were separated by centrifugation. Lanes 1–4—insoluble fraction, lanes 5–8—soluble fraction.

SDS-PAGE analysis of the total cell protein sample from *E. coli* cells harbouring pFGMF1 revealed the presence of a large amount of the fusion protein with molecular mass corresponding to the hGMCSF-Caf1 fusion protein (31 kDa). When the cells were destroyed by sonication this protein was localised in an insoluble fraction (FIG. 12, lane 3, 4).

Figure 13A:
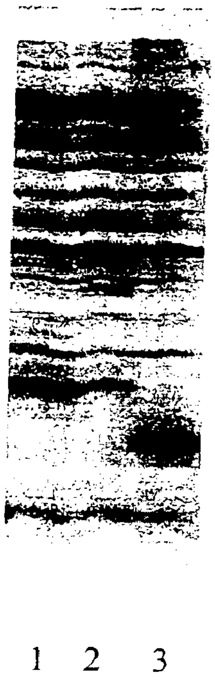
FIG. 13. Expression of scaf1-GMCSF-Caf1 fusion gene. A. SDS-PAGE analysis of periplasmic proteins obtained from cells harboring pFGMF1 (lane 1), pFGMF1 and pCaf1M (lane 2), and pFGM13 (lane 3). B. Protein immonoblot analyzed with anti-GMCSF rabbit polyclonal antibodies. Lanes 1,2—total cell proteins, lanes 3–5—periplasmic proteins. Protein fractions were obtained from cells harboring pFGMF1 (lane 1,4), pFGMF1 and pCaf1M (lane 2,3), and pFGM13 (lane 5). C. lmmonoblot of periplasmic proteins analyzed with anti-Caf1 rabbit polyclonal antibodies. Cells produced GMCSF-Caf1 fusion protein without (lane 1) or with (lane 2) the Caf1M chaperon.
Figure 13B:
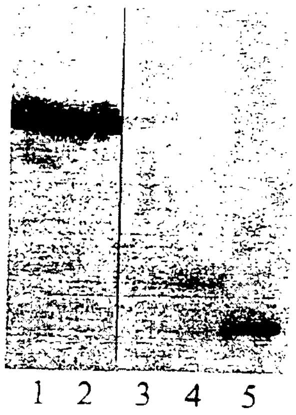
Figure 13C:
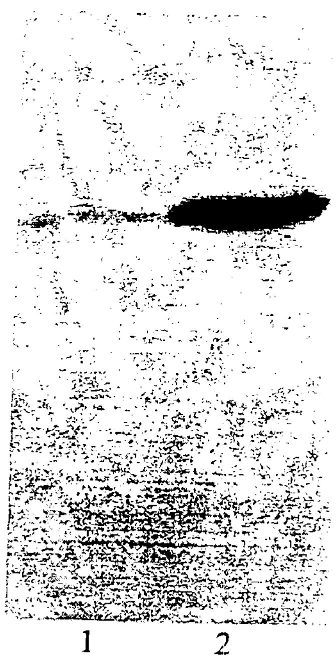

Examination of periplasmic extracts by SDS-PAGE and Western blotting has shown that some hGMCSF-Caf1 fusion was translocated to the periplasm. Its electrophoretic mobility was the same as of the insoluble protein. The fusion interacts with both anti-hGMCSF and anti-Caf1 polyclonal antibodies (FIG. 13B, lanes 1; 14C, lane 1). The protein with molecular weight about 18 kDa was also detected with anti-hGMCSF antibodies (FIG. 13B, lane 4). We can presume that this protein is the product of hGMCSF-Caf1 fusion proteolytic degradation.

To study influence of the Caf1M chaperone on expression of the gmcsf-caf1 gene, the caf1m gene was inserted into the pACYC-trx, a vector with a low copy number and compatible with pBR322-based plasmids. PACYC-trx was pACYC184 derivative that contained trx gene under the control of tac promoter. The Trx coding region, flanked with KpnI and Alw44I sites, was replaced by the DNA fragment coding for the Caf1M chaperone as follows. The caf1m gene was amplified by PCR which included Pfu DNA Polymerase, two primers (GTTGTCGGTACCATTCCGTAAGGAGG (SEQ ID NO: 16) and 5'-GTTAACGTGCACACAGGAACAGC) (SEQ ID NO: 17) and the pFS2 plasmid (Galyov EE et al. (1990) FEBS Letters, 277, 230–232). The PCR fragment was treated with KpnI and Alw44I and cloned into the KpnI-Alw44I large fragment of pACYC-trx. The plasmid obtained was designated as pCaf1M.

JM101 *E. coli* cells were transformed with both pFGMF1 and pCaf1M plasmids followed by analysis of recombinant cell proteins as described above. Co-expression of the chaperone gene from the pCaf1M plasmid led to a marked increase in the amount of the full-length hGMCSF-Caf1 fusion protein in the periplasm (FIG. 13B, lane 3; 13C, lane 2). The amount of 18 kDa protein, the product of hGMCSF-Caf1 fusion proteolytic degradation, decreased. These results demonstrate that Caf1M promotes the correct folding of hGMCSF-Caf1 and enhances the stability of the fusion protein.

EXAMPLE 4

Co-expression of hIL1ra-Caf1 Fusion Protein and the Chaperone

Based on pFGM13, the pFRA275 plasmid was obtained. In this plasmid the 5'-terminal part of the mature hIL-1ra coding region containd AlaAspAsp-coding sequence instead of the first Arg codon in order to neutralise the N-terminal positive charge of hIL1ra. The lac promoter controlled the expression of scaf-hil1ra gene in pFRA275.

The expression plasmid pFRF275 coding for the scaf-hil1ra-caf1 gene was constructed as shown in FIG. 11. At the 3' terminus of the hil1ra gene the Kpn2I site was introduced by PCR of the pFRA275 plasmid with primers 5'-GGAATCCATGGAGGGAAGAT (SEQ ID NO: 18) and 5'-ATTATTCCGGACTCGTCCTCCTGAAAGTAG(SEQ ID NO: 19). The amplified fragment was cut with NcoI and Kpn2I and ligated with the HindIII-Kpn2I large fragment from pFGMF1 together with the HindIII-NcoI fragment from pFRA275. The resulting plasmid (pFRF275) contained a gene which encodes hybrid precursor consisting of the scaf signal sequence, hIl-1ra with amino acid changes mentioned above, a $Ser(4GlySer)_3$ spacer, and Caf1. Plasmid structure was confirmed by restriction analysis and sequencing of amplified regions.

Figure 14A:
FIG. 14. Expression of scaf1-IL1ra-Caf1 fusion gene. A. SDS-PAGE of periplasmic proteins obtained from cells harbouring pFRF275 alone (lane 1) or with pCaf1M (lane 2). B. Immunoblot of the same gel analysed by anti-IL1ra goat polyclonal antibodies.
Figure 14B:
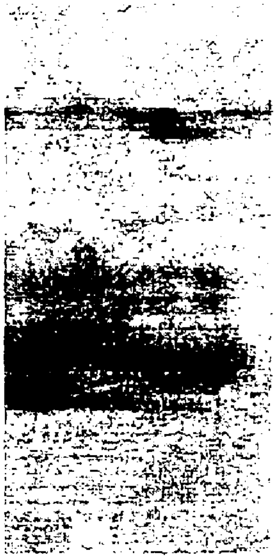

Expression of the scqf-hil1ra-caf1 gene in JM101 *E. coli* cells was analysed as described in EXAMPLE 3. When cells were transformed with pFRF275 alone, the hIL1ra fusion protein accumulated mainly in an insoluble form (35 kDa. FIG. 12, lane 1, 2). However, some part of the fusion protein was translocated to the periplasm, where it was subjected to degradation (FIG. 14B, lane 1). When pFRF275 and pCaf1M (see EXAMPLE 3) were simultaneously present in recombinant cells. Caf1M noticeably diminished the amount of cleavage products (FIG. 14B, lane 2).

What is claimed is:

1. A Gram-negative bacterial strain simultaneously expressing a fusion protein comprising a signal peptide of Caf1, a mature heterologous protein, and a subunit of a bacterial surface structure, which is Caf1 from *Yersinia pestis*, and a periplasmic chaperone Caf1M specific for said subunit for secretion of a recombinant heterologous protein into periplasm of bacteria.

2. The bacterial strain according to claim 1, additionally expressing outer membrane usher or secretin protein Caf1A specific for said subunit, for the purpose of secretion of a soluble recombinant heterologous protein on an outer surface of the bacterium or into cultivation medium of the bacterium.

3. The bacterial strain according to claim 1 or 2, wherein the microbe is *Escherichia coli.*

4. A method for producing a heterologous recombinant protein which is secreted into the periplasm of a bacterium, comprising cultivating a Gram-negative bacterial strain simultaneously expressing a fusion protein comprising a signal peptide of Caf1, a mature heterologous protein, and a subunit of a bacterial surface structure which is Caf1 from *Yersinia pestis*, and a periplasmic chaperone Caf1M specific for said subunit, whereby the recombinant heterologous protein produced is secreted into the periplasm of the bacterium.

5. The method according to claim 4, wherein the heterologous recombinant protein is selected from the group consisting of GMCSF, IL-1β, and IL-1 receptor antagonist.

6. A method for producing a heterologous recombinant protein which is secreted onto the outer surface of a bacterium or into a cultivation medium of a bacterium, comprising the steps of cultivating a Gram-negative bacterial strain simultaneously expressing a fusion protein comprising a signal peptide of Caf1, a mature heterologous protein, and a subunit of a bacterial surface structure which is Caf1 from *Yersinia pestis*, a periplasmic chaperone Caf1M specific for said subunit, and outer membrane usher or secretin protein CalfA specific for said subunit, whereby the recombinant heterologous protein produced is secreted onto the outer surface of the bacterium or into the cultivation medium of the bacterium.

* * * * *

SEQUENCE LISTING

```
<160> NUMBER OF SEQ ID NOS: 25

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Nucleotide
      primer

<400> SEQUENCE: 1

gggaattcag aggtaatata tgaaaaaaat c                                  31


<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Nucleotide
      primer

<400> SEQUENCE: 2

ccgcctgcag atgcggcacc tgtacgatca ctg                                33


<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Nucleotide
      primer

<400> SEQUENCE: 3

ccgcctgcag ttgcaatagt tccaaata                                      28


<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Nucleotide
      primer

<400> SEQUENCE: 4

agaacaccac ttgttgctcc                                               20


<210> SEQ ID NO 5
<211> LENGTH: 37
```

-continued

<212> TYPE: DNA
<213> ORGANISM: Artificial Sequence
<220> FEATURE:
<223> OTHER INFORMATION: Description of Artificial Sequence: Nucleotide primer

<400> SEQUENCE: 5
tggaactatt gcaactgcaa atgcggcacc tgtacga 37

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Nucleotide primer

<400> SEQUENCE: 6
gcaactgcaa atgcggcaga tttagcacct gtacgatcac tg 42

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: Nucleotide primer

<400> SEQUENCE: 7
accggatcca cctccaccag atccacctcc ggaagacaca aattgcatgg 50

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Nucleotide primer

<400> SEQUENCE: 8
ggtggatccg gtggtggtgg atctgcagat ttaactgcaa gcac 44

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Nucleotide primer

<400> SEQUENCE: 9
gccaagcttg tcgacgaggg ttaggctcaa agt 33

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Nucleotide primer

<400> SEQUENCE: 10
tcgacagatc tcgaattccg gtaccggctg ca 32

<210> SEQ ID NO 11
<211> LENGTH: 24
<212> TYPE: DNA

-continued

<213> ORGANISM: Artificial Sequence
<220> FEATURE:
<223> OTHER INFORMATION: Description of Artificial Sequence: Nucleotide
primer

<400> SEQUENCE: 11
gtctagagct taaggccatg gccg 24

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: Nucleotide
primer

<400> SEQUENCE: 12
gatcattaat taat 14

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Nucleotide
primer

<400> SEQUENCE: 13
ccagatctgg caaatattct gaaatg 26

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Nucleotide
primer

<400> SEQUENCE: 14
atcggaaatg ttcgaccttc aag 23

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Nucleotide
primer

<400> SEQUENCE: 15
attattccgg actcctgcac tggttcccag c 31

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Nucleotide
primer

<400> SEQUENCE: 16
gttgtcggta ccattccgta aggagg 26

<210> SEQ ID NO 17
<211> LENGTH: 23
<212> TYPE: DNA
<213> ORGANISM: Artificial Sequence -continued

```
<220> FEATURE:
<223> OTHER INFORMATION: Description of Artificial Sequence: Nucleotide
      primer

<400> SEQUENCE: 17

gttaacgtgc acacaggaac agc                                              23


<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Nucleotide
      primer

<400> SEQUENCE: 18

ggaatccatg gagggaagat                                                  20


<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Nucleotide
      primer

<400> SEQUENCE: 19

attattccgg actcgtcctc ctgaaagtag                                       30


<210> SEQ ID NO 20
<211> LENGTH: 98
<212> TYPE: DNA
<213> ORGANISM: Escherichia coli
<220> FEATURE:
<221> NAME/KEY: CDS
<222> LOCATION: (18)..(98)

<400> SEQUENCE: 20

gaattcagag gtaatat atg aaa aaa atc agt tcc gtt atc gcc att gca        50
                   Met Lys Lys Ile Ser Ser Val Ile Ala Ile Ala
                     1               5                  10

tta ttt gga act att gca act gca gat gcg gca cct gta cga tca ctg       98
Leu Phe Gly Thr Ile Ala Thr Ala Asp Ala Ala Pro Val Arg Ser Leu
            15                  20                  25


<210> SEQ ID NO 21
<211> LENGTH: 27
<212> TYPE: PRT
<213> ORGANISM: Escherichia coli

<400> SEQUENCE: 21

Met Lys Lys Ile Ser Ser Val Ile Ala Ile Ala Leu Phe Gly Thr Ile
  1               5                  10                  15

Ala Thr Ala Asp Ala Ala Pro Val Arg Ser Leu
            20                  25


<210> SEQ ID NO 22
<211> LENGTH: 98
<212> TYPE: DNA
<213> ORGANISM: Escherichia coli
<220> FEATURE:
<221> NAME/KEY: CDS
<222> LOCATION: (18)..(98)

<400> SEQUENCE: 22

gaattcagag gtaatat atg aaa aaa atc agt tcc gtt atc gcc att gca        50
```

-continued

```
                  Met Lys Lys Ile Ser Ser Val Ile Ala Ile Ala
                    1               5                  10

tta ttt gga act att gca act gca aat gcg gca cct gta cga tca ctg        98
Leu Phe Gly Thr Ile Ala Thr Ala Asn Ala Ala Pro Val Arg Ser Leu
            15                  20                  25


<210> SEQ ID NO 23
<211> LENGTH: 27
<212> TYPE: PRT
<213> ORGANISM: Escherichia coli

<400> SEQUENCE: 23

Met Lys Lys Ile Ser Ser Val Ile Ala Ile Ala Leu Phe Gly Thr Ile
  1               5                  10                  15

Ala Thr Ala Asn Ala Ala Pro Val Arg Ser Leu
            20                  25


<210> SEQ ID NO 24
<211> LENGTH: 107
<212> TYPE: DNA
<213> ORGANISM: Escherichia coli
<220> FEATURE:
<221> NAME/KEY: CDS
<222> LOCATION: (18)..(107)

<400> SEQUENCE: 24

gaattcagag gtaatat atg aaa aaa atc agt tcc gtt atc gcc att gca        50
                  Met Lys Lys Ile Ser Ser Val Ile Ala Ile Ala
                    1               5                  10

tta ttt gga act att gca act gca aat gcg gca gat tta gca cct gta        98
Leu Phe Gly Thr Ile Ala Thr Ala Asn Ala Ala Asp Leu Ala Pro Val
            15                  20                  25

cga tca ctg                                                           107
Arg Ser Leu
        30


<210> SEQ ID NO 25
<211> LENGTH: 30
<212> TYPE: PRT
<213> ORGANISM: Escherichia coli

<400> SEQUENCE: 25

Met Lys Lys Ile Ser Ser Val Ile Ala Ile Ala Leu Phe Gly Thr Ile
  1               5                  10                  15

Ala Thr Ala Asn Ala Ala Asp Leu Ala Pro Val Arg Ser Leu
            20                  25                  30
```